United States Patent [19]

Inoue et al.

[11] 4,420,628
[45] Dec. 13, 1983

[54] PROCESS FOR PREPARING THREO-2-HYDROXY-3-(4-METHOXYPHENYL)-3-(2-NITROPHENYLTHIO)-PROPIONIC ESTER

[75] Inventors: Hirozumi Inoue, Oizumi-Gakuen; Tomiki Hashiyama, Ageo, both of Japan

[73] Assignee: Tanabe Seiyaku Co., Ltd., Osaka, Japan

[21] Appl. No.: 346,922

[22] Filed: Feb. 8, 1982

[30] Foreign Application Priority Data

Feb. 27, 1981 [JP] Japan .................................. 56-28779
May 22, 1981 [JP] Japan .................................. 56-78317

[51] Int. Cl.³ .......................................... C07C 149/40
[52] U.S. Cl. .................................. 560/17; 260/429.7
[58] Field of Search .......................................... 560/17

[56] References Cited

FOREIGN PATENT DOCUMENTS 49-36221  9/1974 Japan ..................................... 560/17
49-48305 12/1974 Japan ..................................... 560/17

OTHER PUBLICATIONS

Kugita, Chem. Pharm. Bull., 18, pp. 2028-2037, 2284-2289, (1970).

Primary Examiner—Michael L. Shippen

Attorney, Agent, or Firm—Jordan B. Bierman; Linda Bierman

[57] ABSTRACT

A threo-2-hydroxy-3-(4-methoxyphenyl)-3-(2-nitrophenylthio)propionic ester of the formula:

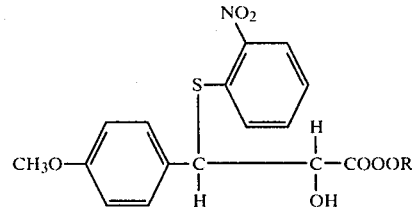

wherein R is an ester residue, is prepared by condensing a trans-3-(4-methoxyphenyl)glycidic ester of the formula:

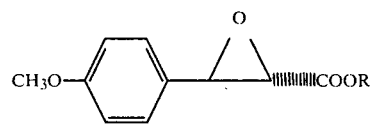

wherein R is the same as defined above, with 2-nitrothiophenol in the presence of a Lewis acid.

6 Claims, No Drawings

PROCESS FOR PREPARING THREO-2-HYDROXY-3-(4-METHOXYPHENYL)-3-(2-NITROPHENYLTHIO)-PROPIONIC ESTER

This invention relates to a novel process for preparing a threo-2-hydroxy-3-(4-methoxyphenyl)-3-(2-nitrophenylthio)propionic ester of the formula:

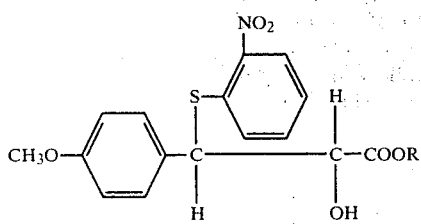

wherein R is an ester residue.

2-Hydroxy-3-(4-methoxyphenyl)-3-(2-nitrophenylthio)propionic ester can exist in the form of two diastereoisomers, i.e., erythro- and threo-isomers, due to the difference in the steric configuration of the hydroxy and nitrophenylthio groups substituted at the 2nd- and 3rd-positions of propionic acid, and the threo isomer (I) thereof (i.e., the compound in which said hydroxy and nitrophenylthio groups have the threo-type configuration) is known to be useful as an intermediate in the synthesis of diltiazem hydrochloride (chemical name: d-3-acetoxy-cis-2,3-dihydro-5-[2-(dimethylamino)ethyl]-2-(p-methoxyphenyl)-1,5-benzothiazepin-4(5H)-one), a $Ca^{++}$-antagonistic coronary vasodilator.

A known method for preparing the compound (I) comprises condensing a trans-3-(4-methoxyphenyl)glycidic ester with 2-nitrothiophenol under nitrogen gas atmosphere in a solvent such as acetonitrile (Japanese Patent Publication (examined) No. 36221/1974, Chem. Pharm. Bull., Vol. 18, p. 2028(1970)). This method gives the compound (I) in a yield of 38 to 56%. However, for industrial scale production of the compound (I) this known method is still unsatisfactory in that it requires a long reaction period such as 68 to 120 hours until completion of said condensation reaction.

On the other hand, Chem. Pharm. Bull., Vol. 18, p.2284 (1970) discloses that the condensation reaction of trans-3-phenylglycidic ester or trans-3-(4-methoxyphenyl)glycidic ester with 2-nitrothiophenol may be carried out in the presence of sodium bicarbonate. Said Chem. Pharm. Bull. also discloses a method of carrying out the condensation of trans-3-phenylglycidic ester and 2-nitrothiophenol in the presence of boron trifluoride. However, these methods give only the erythro isomer of 2-hydroxy-3-(2-nitrophenylthio)-3-phenylpropionic ester or 2-hydroxy-3-(4-methoxyphenyl)-3-(2-nitrophenylthio)propionic ester, and no substantial amount of the desired threo-isomer can be obtained according to said methods. In addition, when the condensation of trans-3-phenylglycidic ester and 2-nitrothiophenol is conducted in the presence of boron trifluoride, the erythro-isomer (i.e., erythro-2-hydroxy-3-(2-nitrophenylthio)-3-phenylpropionic ester) is obtained in an yield of about 15% only.

Unlike the above-mentioned condensation reaction of trans-3-phenylglycidic ester disclosed in said Chem. Pharm. Bull., we have now found that the stereo-selective synthesis of the threo-2-hydroxy-3-(4-methoxyphenyl)-3-(2-nitrophenylthio)propionic ester (I) can be attained successfully by carrying out the condensation reaction of trans-3-(4-methoxyphenyl)glycidic ester and 2-nitrothiophenol in the presence of a Lewis acid such as boron trifluoride. Moreover, quite surprisingly, the Lewis acid present in this reaction system greatly accelerates said condensation reaction, and the threo-isomer (I) is thereby obtained under mild conditions (e.g., at room temperature) and within a remarkably shorter period of time as compared with the method disclosed in Japanese Patent Publication (examined) No. 36221/1974.

According to the present invention, the threo-2-hydroxy-3-(4-methoxyphenyl)-3-(2-nitrophenylthio)-propionic ester (I) can be obtained by condensing a trans-3-(4-methoxyphenyl)glycidic ester of the formula:

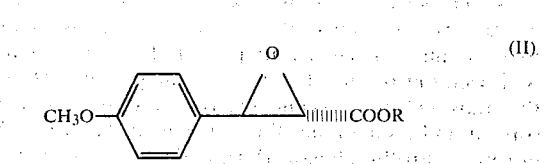

wherein R is the same as defined below, with 2-nitrothiophenol (III) in the presence of a Lewis acid.

A wide variety of Lewis acids can be employed in the method of the present invention. Representative examples of such Lewis acids include boron trifluoride, stannous halide (e.g., stannous fluoride, stannous chloride, stannous bromide, stannous iodide), stannic halide (e.g., stannic fluoride, stannic chloride, stannic bromide, stannic iodide), zinc halide (e.g., zinc chloride, zinc bromide, zinc iodide, zinc fluoride), ferrous halide (e.g., ferrous chloride, ferrous bromide), ferric halide (e.g., ferric chloride, ferric bromide), cuprous halide (e.g., cuprous chloride, cuprous bromide), cupric halide (e.g., cupric chloride, cupric bromide), antimony trihalide (e.g., antimony trichloride, antimony tribromide), antimony pentahalide (e.g., antimony pentachloride, antimony pentabromide), cadmium halide (e.g., cadmium chloride, cadmium bromide), nickel halide (e.g., nickel chloride, nickel bromide), stannous alkanoate (e.g., stannous acetate, stannous octylate, stannous stearate), stannic alkanoate (e.g., stannic octylate), zinc alkanoate (e.g., zinc acetate, zinc stearate), zinc salicylate, zinc oxalate, sulfuric acid, perhalogenic acid (e.g., perchloric acid, perbromic acid, periodic acid), alkanoic acid (e.g., acetic acid, trifluoroacetic acid, propionic acid), aromatic carboxylic acid (e.g., benzoic acid), sulfonic acid (e.g., methanesulfonic acid, benzenesulfonic acid, p-toluenesulfonic acid), phosphoric acid and polyphosphoric acid. Among these Lewis acids, a preferred subgenus include boron trifluoride (or its etherate), stannous halide (e.g., stannous fluoride, stannous chloride, stannous bromide, stannous iodide), stannic halide (e.g., stannic fluoride, stannic chloride, stannic bromide, stannic iodide), zinc halide (e.g., zinc chloride, zinc bromide, zinc fluoride, zinc iodide), stannous alkanoate (e.g., stannous acetate, stannous octylate, stannous stearate), stannic alkanoate (e.g., stannic octylate), zinc alkanoate (e.g., zinc acetate, zinc stearate), zinc salicylate, zinc oxalate, perhalogenic acid (e.g., perchloric acid, perbromic acid) and sulfuric acid. More preferred subgenus include boron trifluoride (or it etherate), stannous chloride, stannous fluoride, stannous bromide, stannous iodide, stannic chloride, stannic bromide, stannic iodide, zinc chloride, stannous octylate, stannous stearate, stannic octylate, zinc acetate, perchloric acid and sulfuric acid.

The ester residue (R) of the starting compound (II) may be either alkyl, aryl or aralkyl groups. Among them, alkyl of one to 4 carbon atoms such as methyl, ethyl, propyl or butyl is especially suitable as the ester residue of the compound (II).

The condensation of the compound (II) with the compound (III) is readily accomplished in a solvent. Ether, tetrahydrofuran, isopropyl ether, dimethoxyethane, dioxane, benzene, toluene, acetonitrile, chloroform, acetone, carbon tetrachloride, and the like are suitably used as the solvent. In carrying out the reaction, the starting compounds and Lewis acid may be added in any order to the solvent. From a practical viewpoint such as for the sake of the convenience of operations or in view of the yield of the threo-isomer (I) to be obtained, it is generally preferred that the reaction is carried out by dissolving 2-nitrothiophenol (III) and the trans-3-(4-methoxyphenyl)glycidic ester (II) in the solvent and then adding the Lewis acid thereto, or by mixing 2-nitrothiophenol (III) and the Lewis acid in the solvent and then adding the trans-3-(4-methoxyphenyl)glycidic ester (II) to the mixture. It is also preferable to carry out the reaction at a temperature in the range of from 0° to 80° C., especially in the range of from 10° to 50° C. Though the reaction speed may vary depending on particular conditions used such as Lewis acid, reaction temperature and so forth, said condensation reaction is completed within about 5 minutes to about 20 hours and in most of cases within 5 minutes to 10 hours.

Alternatively, when a stannous or stannic compound of the formula: $SnX_q$ (IV) (wherein X is halogen or alkanoyloxy, and q is an integer 2 or 4) is used as the Lewis acid, the above-mentioned condensation reaction of the invention may be conducted by first reacting said stannous or stannic compound (IV) with 2-nitrothiophenol (III) to give a compound of the formula:

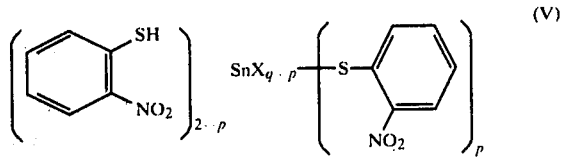

(V)

wherein p is an integer of 0, 1 or 2, and X and q are the same as defined above, and then using compound (V) as a catalyst or as one of the starting compounds instead of 2-nitrothiophenol (III). In this case, the threo-2-hydroxy-3-(4-methoxyphenyl)-3-(2-nitrophenylthio)-propionic ester (I) is prepared by (i) reacting the compound (V) directly with the trans-3-(4-methoxyphenyl)glycidic ester (II), or (ii) condensing the trans-3-(4-methoxyphenyl)glycidic ester (II) with 2-nitrothiophenol (III) in the presence of a catalytic amount of the compound (V).

The stannous or stannic compound (IV) which can be used for this purpose includes, for example, stannous halide (e.g., stannous fluoride, stannous chloride, stannous bromide, stannous iodide), stannic halide (e.g., stannic fluoride, stannic chloride, stannic bromide, stannic iodide), stannous alkanoate (e.g., stannous octylate, stannous stearate) and stannic alkanoate (e.g., stannic octylate, stannic stearate).

The reaction of the stannous or stannic compound (IV) with 2-nitrothiophenol (III) is accomplished in a suitable solvent. Examples of the solvent include benzene, toluene, xylene, n-pentane, n-hexane, cyclohexane, cycloheptane and mixtures thereof. In carrying out the reaction, it is preferred to use 2 to 3 moles of 2-nitrothiophenol (III) per mole of the stannous or stannic compound (IV). It is also preferred to carry out the reaction at a temperature of −30° to 60° C., especially 0° to 25° C. When stannic halide or stannic alkanoate is used as the compound (IV), the following compound (V-a), (V-b), (V-c), or a mixture thereof is obtained. Especially when stannic halide is used as the compound (IV), the following compound (V-b) (X=halogen) is obtained preferably as a main product.

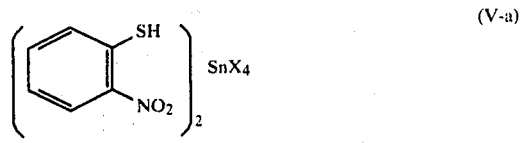

(V-a)

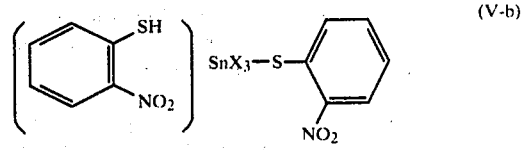

(V-b)

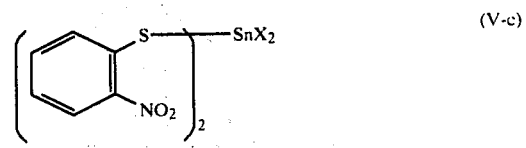

(V-c)

(In the above-mentioned formulas, X is the same as defined above.)

On the other hand, the following compound (V-d), (V-e) or (V-f) or a mixture thereof is obtained when stannous halide or stannous alkanoate is used as the compound (IV).

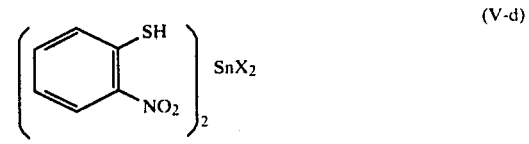

(V-d)

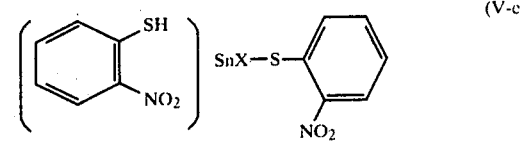

(V-e)

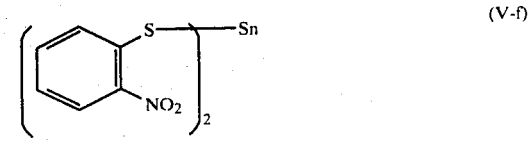

(V-f)

(In the above-mentioned formulas, X is the same as defined above.)

The subsequent condensation reaction of the compound (V) with the trans-3-(4-methoxyphenyl)glycidic ester (II) is conducted in a solvent. Benzene, toluene, xylene, cyclohexane, cycloheptane or a mixture thereof are suitable as the solvent. It is preferable to carry out the reaction at a temperature in the range of from 0° to 60° C., especially in the range of from 10° to 25° C.

Generally, the reaction is completed within 10 minutes to one hour. On the other hand, the condensation of the trans-3-(4-methoxyphenyl)glycidic ester (II) and 2-nitrothiophenol (III) in the presence of a catalytic amount of the compound (V) may also be readily conducted in a solvent. Examples of the solvent include benzene, toluene, xylene, cyclohexane, cycloheptane, dioxane, tetrahydrofuran and mixtures thereof. In this latter case, it is preferable to use 0.005 to 0.01 mole of the compound (V) per mole of 2-nitrothiophenol (III). It is also preferable to carry out the reaction at a temperature in the range of from 0° to 60° C., especially in the range of from 10° to 25° C. Generally, the reaction may be completed within 4 to 20 hours.

The compound (I) thus obtained can be converted to diltiazem hydrochloride, for example, in accordance with the methods described in Japanese Patent Publication (examined) Nos. 27576/1974 and 18038/1978.

As mentioned hereinbefore, Chem. Pharm. Bull., Vol. 18, p.2284(1970) discloses a method of condensing trans-3-phenylglycidic ester with 2-nitrothiophenol in the presence of boron trifluoride. According to this known method, said trans-3-phenylglycidic ester causes trans opening of oxirane ring to give an erythro isomer, i.e., erythro-2-hydroxy-3-(2-nitrophenylthio)-3-phenyl-propionic ester. In condensing the trans-3-(4-methoxyphenyl)glycidic ester (II) with 2-nitrothiophenol, however, cis-opening of the glycidate occurs even in the presence of boron trifluoride or other Lewis acids due to the electronic effect of the substituent on the phenyl group thereof, thereby giving threo-2-hydroxy-3-(4-methoxyphenyl)-3-(2-nitrophenylthio)propionic ester quite exclusively. In addition, while in the method of said literature the erythro isomer could be obtained in an yield of only about 15%, the method of the present invention gives the threo isomer (I) in an yield of about 40 to about 75% and said yield of the invention is almost comparable to or somewhat superior to the yield of the compound (I) obtained by the method of Japanese Patent Publication (examined) No 36221/1974 (i.e., the method wherein the condensation reaction is carried out in the absence of the catalyst). Moreover, though one of the technical disadvantages of the method of said Japanese Patent Publication (examined) No. 36221/1974 was that it requires a long reaction period such as 68 to 120 hours to complete the reaction, the method of the present invention makes it possible to complete the reaction within a shorter period of time such as within about 20 hours and in most of cases within 5 minutes to 10 hours. In contrast to the prior teachings shown in the Chem. Pharm. Bull. referred to above, therefore, the addition of a Lewis acid to the condensation reaction system of the glycidate (II) and 2-nitrothiophenol (III) accelerates said reaction quite efficiently and at the same time, as compared with the method of Japanese Patent Publication (examined) No. 36221/1974, the method of the present invention is more advantageous for the production of the threo-2-hydroxy-3-(4-methoxyphenyl)-3-(2-nitrophenylthio)-propionic ester (I) on an industrial scale.

Practical and presently-preferred embodiments of the present invention are shown in the following Examples. Throughout the specification and claims, the term "threo" means that the hydroxy and 2-nitrophenylthio groups substituted at the 2nd- and 3rd-positions of propionic acid have threo-type configuration (i.e., said two groups are placed on opposite sides of the central bond in the Fisher's projection formula), and the term "erythro" means that said hydroxy and 2-nitrophenylthio groups have erythro-type configuration (i.e., said two groups are placed on the same side of the central bond). In this respect, it should be noted that the stereochemical nomenclature used in Chem. Pharm. Bull., Vol. 18, p.2284(1974) is different from that of the present invention because the terms "erythro" and "threo" in said literature have been named based on the relative configuration of the hydroxy and pheny groups substituted at the 2nd- and 3rd-positions of propionic acid. Therefore, the term "threo" in this specification and claims corresponds exactly to the term "erythro" in the above-mentioned literature, and the term "erythro" in this specification and claims to "threo" in said literature, respectively. Concomitantly, throughout the specification and claims, the terms "alkanoate," "alkanoic acid" and "alkanoyl" should be interpreted as referring to alkanoate, alkanoic acid and alkanoyl having 2 to 18 carbon atoms, respectively.

EXAMPLE 1

2 g of 2-nitrothiophenol are dissolved in anhydrous ether, and 0.1 ml of boron trifluoride etherate is added thereto in an argon gas atmosphere. The solution is cooled to 10° C., and 3.2 g of methyl trans-3-(4-methoxyphenyl)glycidate are added dropwise to the solution at the same temperature for about 15 minutes. The mixture is then stirred at 16° to 20° C. for 20 minutes. After the reaction, the mixture is evaporated under reduced pressure to remove solvent. 20 ml of ethanol-isopropyl ether (1:1) are added to the crystalline residue, and the mixture is admixed well. Then, the mixture is ice-cooled for 20 minutes. The resultant crystals are collected by filtration, washed with 10 ml of ethanol-isopropyl ether (1:1) and with ether, and then dried. 2.39 g of methyl threo-2-hydroxy-3-(4-methoxyphenyl)-3-(2-nitrophenylthio)-propionate are obtained. Yield: 51.3%

M.p. 154°–156° C.

EXAMPLE 2

2 g of 2-nitrothiophenol and 3.2 g of methyl trans-3-(4-methoxyphenyl)glycidate are dissolved in 10 ml of anhydrous ether, and a solution of 0.1 ml of boron trifluoride etherate in 10 ml of anhydrous ether is added at 10° C. to the solution in argon gas atmosphere for about 10 minutes. The mixture is stirred at the same temperature for 10 minutes. After the reaction, the mixture is treated in the same manner as described in Example 1. 2.435 g of methyl threo-2-hydroxy-3-(4-methoxyphenyl)-3-(2-nitrophenylthio)propionate are obtained. Yield: 52.2%.

The physico-chemical properties of the product are identical with those of the sample obtained in Example 1.

EXAMPLES 3–21

2-Nitrothiophenol is reacted with methyl trans-3-(4-methoxyphenyl)glycidate in the presence of a Lewis acid shown in Table 1. The reaction is carried out in the same manner as described in Example 1 or 2. Methyl threo-2-hydroxy-3-(4-methoxyphenyl)-3-(2-nitrophenylthio)propionate is thereby obtained as shown in Table 1.

TABLE 1

| Example Nos. | Lewis acid | Solvent | Reaction temperature (°C.) | Reaction period | Yield (%) |
|---|---|---|---|---|---|
| 3. | $SnCl_2$ | toluene | 23 | 7.5 hr | 65.7 |
| 4. | " | dioxane | 23 | 21 hr | 68.5 |
| 5. | $SnI_2$ | " | 23 | 17 hr | 67.5 |
| 6. | $SnF_2$ | " | 23 | 22.5 hr | 71.5 |
| 7. | $SnCl_4$ | " | 23 | 4 hr | 63.2 |
| 8. | " | " | 10 | 1 hr | 68.5 |
|  |  |  | 23 | 18 hr |  |
| 9. | $SnBr_4$ | " | 23 | 20 hr | 63.0 |
| 10. | $SnI_4$ | " | 23 | 22.5 hr | 65.2 |
| 11. | $Sn(C_7H_{15}COO)_2$ | " | 23 | 19 hr | 73.6 |
| 12. | $Sn(C_7H_{15}COO)_4$ | " | 23 | 8 hr | 50.4 |
| 13. | $Sn(C_{17}H_{35}COO)_2$ | " | 50 | 2 hr | 66.6 |
| 14. | $ZnCl_2$ | " | 10 | 50 min | 50.1 |
|  |  |  | 15 | 20 min |  |
| 15. | $BF_3 \cdot (C_2H_5)_2O$ | benzene | 10 | 15 min | 45.7 |
| 16. | " | dioxane | 10 | 5 min | 51.0 |
| 17. | " | toluene | 10 | 15 min | 49.7 |
| 18. | " | dimethoxyethane | 10 | 5 min | 49.7 |
| 19. | " | acetone | 10 | 1 hr | 43.6 |
|  |  |  | 23 | 1 hr |  |
| 20. | conc. $H_2SO_4$ | dioxane | 10 | 10 min | 41.3 |
| 21. | 70% $HClO_4$ | " | 10 | 10 min | 47.6 |

EXAMPLE 22

14 g of 2-nitrothiophenol are dissolved in 70 ml of toluene, and 0.05 g of zinc acetate dihydrate is added thereto. The mixture is stirred at room temperature for 5 minutes. Then, 19.7 g of methyl trans-3-(4-methoxyphenyl)glycidate are added to the mixture, and said mixture is stirred at room temperature for 6 to 7 hours. After the reaction, the resultant crystals are collected by filtration. The crystals thus obtained are treated in the same manner as described in Example 1. 24.3 g of methyl threo-2-hydroxy-3-(4-methoxyphenyl)-3-(2-nitrophenylthio)propionate are obtained. Yield: 74.1%.

The physico-chemical properties of the product are identical with those of the sample obtained in Example 1.

EXAMPLE 23

(1) 33.05 g (0.213 mole) of 2-nitrothiophenol are dissolved in 30 ml of anhydrous benzene, and the solution is cooled to 10° C. A solution of 25.0 g (0.0968 mole) of stannic chloride in 50 ml of anhydrous benzene is added dropwise to the solution for 30 minutes, and the mixture is stirred at 10° C. for one hour. Insoluble materials are removed by filtration, and washed with anhydrous benzene. The filtrate and the washings are combined and evaporated under reduced pressure to remove solvent. 100 ml of a mixture of anhydrous benzene and n-hexane (3:1) are added to the residue, and crystalline precipitates are collected by filtration. 15.6 g of yellow crystals (M.p. 138°–143° C. (decomp.)) obtained and are recrystallized from anhydrous benzene. 8.8 g of the crystalline adduct of stannic chloride and 2-nitrothiophenol are obtained.

Analysis calculated for $C_{12}H_9N_2O_4S_2SnCl_3$: C, 26.97; H, 1.70; N, 5.24; S, 12.00; Found: C, 27.13; H, 1.71; N, 5.32; S, 12.06.

Mass spectrum (m/e):

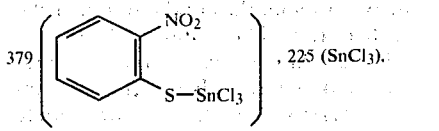

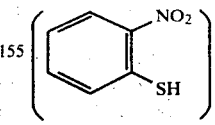

NMR spectrum (δ, $CDCl_3$): 4.05 (s, 1H), 7.26–8.35 (m, 8H).

IR spectrum (cm$^{-1}$, $CHCl_3$): 2600, 1585, 1570, 1510, 1460, 1340, 1305, 1260, 1140, 1115, 1010, 855.

These physico-chemical data suggest that this adduct has a chemical structure shown by the following formula:

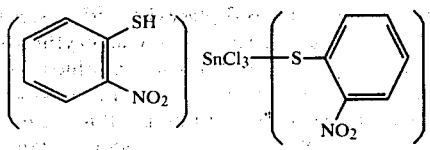

(2) 1.5 g (0.0028 mole) of the stannic chloride 2-nitrothiophenol adduct obtained in paragraph (1) are dissolved in 10 ml of anhydrous benzene, and 0.584 g (0.0028 mole) of methyl trans-3-(4-methoxyphenyl)glycidate is added at room temperature thereto. The mixture is stirred at room temperature for 10 minutes. After the reaction, the mixture is evaporated under reduced pressure to remove solvent. The residue thus obtained is adsorbed to 60 g of silica gel packed in a column, and the column is eluted with a mixture of benzene and ethyl acetate (15:1). The eluates are combined and evaporated to remove solvent. Then, the crystals (0.69 g) thus obtained are washed with benzene. 0.48 g of methyl threo-2-hydroxy-3-(4-methoxyphenyl)-3-(2-nitrophenylthio)propionate is obtained. Yield: 47.1%.

M.p. 154°–156° C.

EXAMPLE 24

2 g (0.013 mole) of 2-nitrothiophenol are dissolved in 20 ml of anhydrous toluene. 0.06 g of the stannic chloride 2-nitrothiophenol adduct obtained in Example 23-(1) is added to the solution at room temperature, and 3.2 g (0.0155 mole) of methyl trans-3-(4-methoxyphenyl)glycidate are further added thereto at room temperature. The mixture is stirred at room temperature for 17 hours. After the reaction, the crystalline precipitates are collected by filtration, washed with anhydrous benzene and dried. 3.18 g of methyl threo-2-hydroxy-3-(4-methoxyphenyl)-3-(2-nitrophenylthio)propionate are thereby obtained. Yield: 67.9%.

M.p. 154°–156° C.

EXAMPLE 25

(1) 2-nitrothiophenol and stannous chloride are treated in the same manner as described in Example 23-(1), whereby the adduct of stannous chloride and 2-nitrothiophenol is obtained.

(2) 2-nitrothiophenol is reacted with methyl trans-3-(4-methoxyphenyl)glycidate in the presence of the stannous chloride 2-nitrothiophenol adduct obtained in paragraph (1). Said reaction is carried out in the same manner as described in Example 24. Methyl threo-2-hydroxy-3-(4-methoxyphenyl)-3-(2-nitrophenylthio)-propionate is thereby obtained. Yield: 63%

EXAMPLE 26

(1) 2-nitrothiophenol and stannous octylate are treated in the same manner as described in Example 23-(1), whereby the adduct of stannous octylate and 2-nitrothiophenol is obtained.

(2) 2-nitrothiophenol is reacted with methyl trans-3-(4-methoxyphenyl)glycidate in the presence of the stannous octylate 2-nitrothiophenol adduct obtained in paragraph (1). Said reaction is carried out in the same manner as described in Example 24. Methyl threo-2-hydroxy-3-(4-methoxyphenyl)-3-(2-nitrophenylthio)-propionate is thereby obtained. Yield: 68%.

What we claim is:

1. A method for preparing a threo-2-hydroxy-3-(4-methoxyphenyl)-3-(2-nitrophenylthio)propionic ester of the formula:

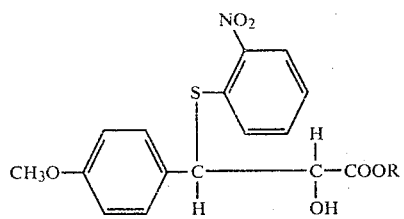

wherein R is an ester residue, which comprises condensing a trans-3-(4-methoxyphenyl)glycidic ester of the formula:

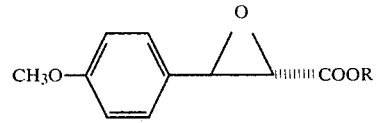

wherein R is the same as defined above, with 2-nitrothiophenol in the presence of a Lewis acid selected from the group consisting of boron trifluoride, stannous halide, stannic halide, zinc halide, ferrous halide, ferric halide, cuprous halide, cupric halide, antimony trihalide, antimony pentahalide, cadmium halide, nickel halide, stannous alkanoate, stannic alkanoate, zinc alkanoate, zinc salicylate, zinc oxalate, sulfuric acid, perhalogenic acid, alkanoic acid, aromatic carboxylic acid, sulfonic acid, phosphoric acid and polyphosphoric acid.

2. The method according to claim 1, wherein the Lewis acid is selected from the group consisting of boron trifluoride, stannous halide, stannic halide, zinc halide, stannous alkanoate, stannic alkanoate, zinc alkanoate, zinc salicylate, zinc oxalate, perhalogenic acid and sulfuric acid.

3. The method according to claim 1, wherein the Lewis acid is selected from the group consisting of boron trifluoride, stannous chloride, stannous fluoride, stannous bromide, stannous iodide, stannic chloride, stannic bromide, stannic iodide, zinc chloride, stannous octylate, stannous stearate, stannic octylate, zinc acetate, perchloric acid and sulfuric acid.

4. The method according to claim 1, 2, or 3, wherein the ester residue (R) is alkyl of one to 4 carbon atoms.

5. The method according to claim 4, wherein the condensation is carried out in a solvent at a temperature in the range of from 0° to 80° C.

6. The method according to claim 4, wherein the condensation is carried out in a solvent at a temperature in the range of from 10° to 50° C.

* * * * *